(12) United States Patent
Ranner

(10) Patent No.: US 7,168,901 B2
(45) Date of Patent: Jan. 30, 2007

(54) DEVICE AND METHOD FOR TRIMMING SAMPLES

(75) Inventor: Robert Ranner, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 0 days.

(21) Appl. No.: 10/905,487

(22) Filed: Jan. 6, 2005

(65) Prior Publication Data

US 2005/0152760 A1    Jul. 14, 2005

(30) Foreign Application Priority Data

Jan. 8, 2004    (DE)   ................ 10 2004 001 475

(51) Int. Cl.
| | |
|---|---|
| B23D 5/00 | (2006.01) |
| B23Q 1/25 | (2006.01) |
| B26D 7/06 | (2006.01) |

(52) U.S. Cl. ............... 409/293; 409/131; 409/135; 83/72; 83/713; 83/915.5

(58) Field of Classification Search ........... 409/293, 409/301, 303, 304, 80, 131, 135; 407/113, 407/114, 115, 116, 117; 82/118, 120, 121, 82/129; 29/39, 40, 41, 30, 27 C, 37 R, 37 A, 29/35.5; 83/915.5, 72, 713, 412, 414, 714, 83/717, 718, 703

See application file for complete search history.

(56) References Cited

U.S. PATENT DOCUMENTS

| | | | | |
|---|---|---|---|---|
| 3,621,752 A | | 11/1971 | Sitte ........................ 90/11 |
| 4,101,405 A | * | 7/1978 | Inoue ...................... 409/165 |
| 4,738,170 A | * | 4/1988 | Isawa et al. ............... 82/122 |
| 5,361,472 A | * | 11/1994 | Kubota ..................... 82/120 |
| 5,538,372 A | * | 7/1996 | Cuneo et al. ............. 409/131 |
| 5,752,425 A | | 5/1998 | Asakura et al. ............ 83/713 |
| 5,906,148 A | | 5/1999 | Aihara et al. .............. 83/72 |
| 6,382,886 B1 | * | 5/2002 | Jaeger ..................... 409/131 |
| 6,422,793 B1 | * | 7/2002 | Todisco et al. ........... 409/304 |
| 6,655,245 B2 | * | 12/2003 | Schuettel ................. 409/135 |
| 6,733,214 B2 | * | 5/2004 | Scherbarth ................ 407/113 |

FOREIGN PATENT DOCUMENTS

| | | |
|---|---|---|
| DE | 1 865 284 | 1/1963 |
| DE | 7 009 374 | 3/1970 |
| GB | 1254047 | 11/1971 |
| JP | 55-022149 | 2/1980 |

OTHER PUBLICATIONS

Leica Mikrosysteme GmbH, Leica EM TRIM Specimen Trimmer, Apr. 1994 and Mar. 1998, Vienna, Austria.

Leica Mikrosysteme Aktiengesellschaft, Leica EM FCS Low Temperature Sectioning System, Apr. 1999, Vienna, Austria.

* cited by examiner

*Primary Examiner*—Dana Ross
(74) *Attorney, Agent, or Firm*—Simpson & Simpson, PLLC

(57) ABSTRACT

A device 1 and a method for trimming samples 38 are disclosed. The device 1 encompasses a knife holder 9 and a sample holder 7, the knife holder 9 carrying at least one trimming knife 36. A first motor 60 and a second motor 61 are provided, which move the knife holder 9 in an X-Y plane. Also provided is a control unit 15 that controls the motion of the knife holder 9. The first and the second motor 60, 61 are each equipped with a measurement means 62, 63 that measures the position of the knife holder 9 in the X direction (X) and Y direction (Y).

13 Claims, 6 Drawing Sheets

DEVICE AND METHOD FOR TRIMMING SAMPLES

CROSS REFERENCE TO RELATED APPLICATIONS

This application claims priority of the German patent application 10 2004 001 475.2, filed Jan. 8, 2004, which is incorporated by reference herein.

FIELD OF THE INVENTION

The invention concerns a device for trimming samples and the invention further concerns a method for trimming samples.

BACKGROUND OF THE INVENTION

Microtomes and ultramicrotomes are, as a rule, equipped with at least one knife that serves for the production of thin sections of a sample. Microtomes and/or ultramicrotomes are enclosed in the region of the knife holder and the sample holder, as applicable, by a cooling chamber. The samples can then be produced in thin sections at low temperatures. Before the samples can be sectioned, they are trimmed in suitable fashion.

For sectioning at room temperature, trimming machines that are equipped with a milling cutter are known from the existing art (see Leica EM TRIM brochure). With the trimming machine, the specimen is shaped into the form of a four-sided pyramid. The tip of the pyramid is then milled down. This surface then constitutes the (usually rectangular) precut surface or front surface proceeding from which the thin sections are produced.

If sectioning is performed at low temperature in a cooling chamber, however, it is not possible to use an external trimming device at room temperature. The purpose of the invention is to develop a trimming method for low-temperature applications that can proceed automatically.

With the Leica EM FCS cooling chamber ("Low-Temperature Sectioning System" brochure), trimming takes place in the cooling chamber. The trimming knife is used both to shape the specimen on the sides and also to cut across the front surface of the sample. After a rotation of the sample, the two side surfaces are shaped in turn. The result is to produce a rectangular precut surface, or the front surface. The trimming operation encompasses bringing the trimming knife close, precutting the front surface, laterally displacing the trimming knife, shaping the side surface, displacing the trimming knife to the other side of the sample, shaping the other side surface, rotating the sample 90°, displacing the trimming knife, shaping the side surface, displacing the trimming knife again, and shaping the fourth side surface. The method just described according to the existing art can take up to an hour, and therefore usually takes longer than the actual production of thin sections. The user must set the individual steps on the unit, and is thus "tied" to the unit for sample trimming and cannot perform any other work. Only sectioning of the sample is motorized.

SUMMARY OF THE INVENTION

It is therefore the object of the present invention to create a device with which thin sections of a sample can be produced quickly at low temperatures. The intention is also for the trimming operation to proceed quickly and with as little oversight as possible by the user.

This object is achieved, according to the present invention, by way of a device for trimming samples: comprising a knife holder and a sample holder, wherein the knife holder carries at least one trimming knife and a cutting knife, a cooling chamber surrounds the sample holder and the knife holder; a first motor is provided that moves the knife holder in the X direction, a second motor is provided that moves the knife holder in the Y direction; a control unit associated with the device, wherein the control unit controls the motion of the knife holder in the X direction and the motion of the knife holder in the Y direction; and a measurement means is provided with the first and the second motor which measures the position of the knife holder in the X direction and Y direction.

A further object of the invention is to create a method with which thin sections of a sample can be produced quickly at low temperatures. The intention is also for the trimming operation to proceed quickly and with as little oversight as possible by the user.

This object is achieved, according to the present invention, by way of a method for trimming samples, comprises the steps of:

providing a knife holder and a sample holder, wherein the knife holder carries at least one trimming knife and a cutting knife and a cooling chamber surrounds the sample holder and the knife holder;

moving the knife holder in the X direction with a first motor and in the Y direction with a second motor;

moving the trimming knife with the first and the second motor in the X direction and Y direction to a starting point against a front surface of the sample, and storing that position and inputting the trimming depth by pressing a button;

moving the trimming knife with the first and the second motor to a starting point at a right side of the sample, and storing that position and inputting the trimming depth by pressing a button;

moving the trimming knife with the first and the second motor to a starting point at a left side of the sample, and storing that position and inputting the trimming depth by pressing a button;

actuating a start button on the control unit in order to start the automatic generation of the respective side surfaces of the sample.

The invention has the advantage that a first motor is provided that moves the knife holder in the X direction, and a second motor is provided that moves the knife holder in the Y direction; that the device has associated with it a control unit that controls the motion of the knife holder in the X direction and the motion of the knife holder in the Y direction; and that the first and the second motor are equipped with a measurement means that measures the position of the knife holder in the X direction and Y direction.

The first and the second motor are embodied as stepping motors, and that the measurement means for determining the position of the knife holder counts the steps of the first and the second motor in the X direction and Y direction.

The trimming knife inserted into the knife holder possesses a first cutting edge, a second cutting edge, and a third cutting edge. The second cutting edge generates a front surface on the sample, the second cutting edge being parallel to the front surface of the sample. The first cutting edge generates at least one right side surface of the sample. The third cutting edge generates at least one left side surface of the sample.

The method for trimming samples is advantageous because it encompasses the steps of moving the knife holder in the X direction with a first motor and in the Y direction with a second motor; inputting at least one starting position and a trimming depth associated therewith, for generating at least one side surface on the sample; and actuating a start button on the control unit in order to start the automatic generation of the at least one side surface of the sample.

A further advantage is that a first side surface, a second side surface, a third side surface, a fourth side surface, and a front surface are automatically generated on the sample. The trimming knife is embodied with a first cutting edge, a second cutting edge, and a third cutting edge. The first side surface, second side surface, third side surface, and fourth side surface of the sample are configured using the first cutting edge and the third cutting edge. The fifth side surface, which is referred to as the front surface, is configured using the second cutting edge of the trimming knife.

The knife holder exhibits a first and a second position, the trimming knife being used in the first position and a sectioning knife in the second position; and that the knife holder is pivotable about an axis so that after trimming of the sample, the sectioning knife is pivoted into a position opposite the trimmed sample with no need to remove the knife holder from the cooling chamber.

BRIEF DESCRIPTION OF THE DRAWINGS

Further advantages and advantageous embodiments of the invention may be inferred from the dependent claims, and are the subject matter of the Figures below and their descriptions. In the individual Figures:

DETAILED DESCRIPTION OF THE INVENTION

Figure 1:
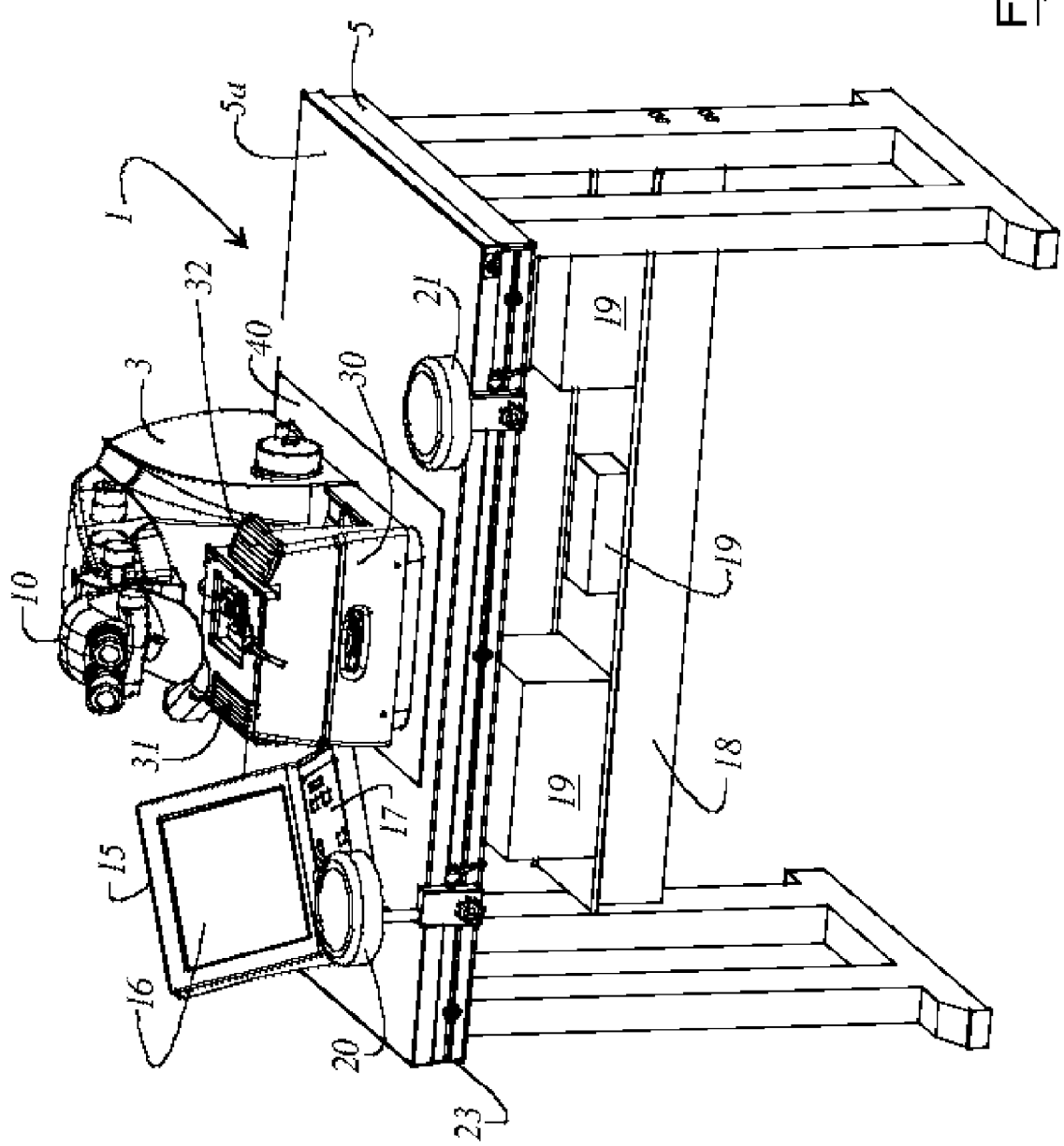
FIG. 1 is a perspective view of a device for sectioning samples.

FIG. 1 is a perspective view of a device 1 for sectioning and trimming samples at low temperatures. Device 1 encompasses a sectioning apparatus 3 for generating thin sample pieces, and a cooling chamber 30 that encloses at least sample holder 7 and knife holder 9. Sectioning apparatus 3 and cooling chamber 30 are placed on a table 5. Sectioning apparatus 3 carries knife holder 9 and sample holder 7. Displaceable arm supports 20 and 21 are provided on table 5 opposite knife holder 9 and sample holder 7. Arm supports 20 and 21 are adjustable to a user's ergonomics and to a configuration of the device. Table 5 is equipped with a vibration-damping insert 40 on which sectioning apparatus 3 and cooling chamber 30 stand. A control unit 15 for controlling and regulating sectioning apparatus 3 and cooling chamber 30 is additionally provided on table 5. Control unit 15 encompasses a display 16 and an input unit 17. Provided beneath table surface 5a of table 5 is a platform 18 on which electronics and power-supply modules 19 are placed. As is evident from FIG. 1, a rail 23 is mounted on table 5 opposite knife holder 9 and sample holder 7. Arm supports 20 and 21 are mounted in horizontally displaceable fashion in rail 23. A stereomicroscope 10 is provided on sectioning apparatus 3 for observation of the sectioning operation by the user. Cooling chamber 30 likewise has supports 31 and 32 for a user's hands. When a microtome or ultramicrotome is used as sectioning apparatus 3 together with a cooling chamber 30, the user rests his or her hands on supports 31 and 32 on cooling chamber 30, and supports his or her elbows on arm supports 20 and 21 of table 5.

Figure 2:
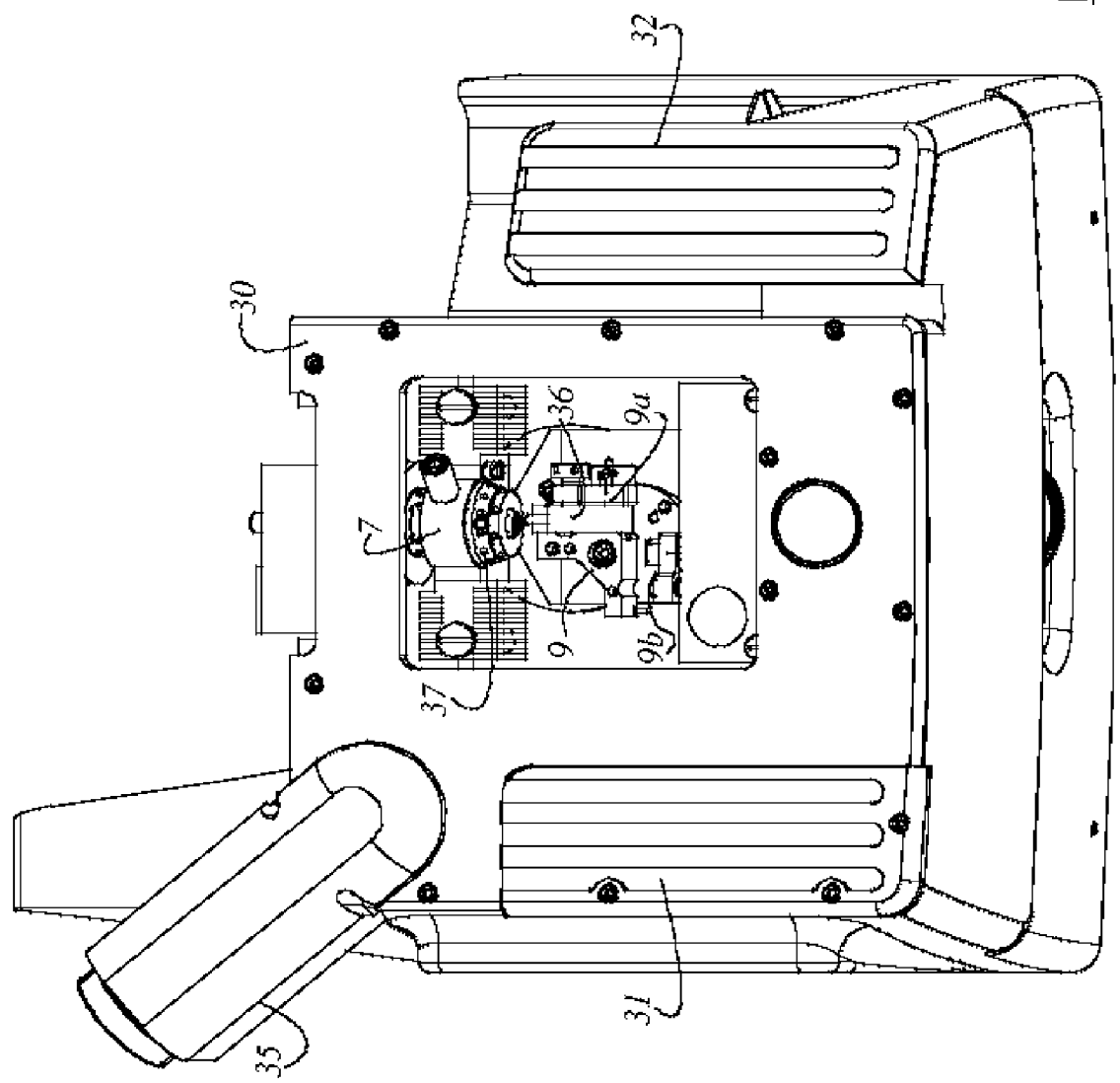
FIG. 2 is a detailed view of a cooling chamber for sectioning samples at low temperatures.

FIG. 2 is a detailed view of cooling chamber 30 for sectioning samples at low temperatures. Cooling chamber 30 encompasses supports 31 and 32 for the user's hands. Cooling chamber 30 is furthermore equipped with a connector element 35 for delivery of a coolant. Cooling chamber 35 encloses sample holder 7 and knife holder 9. Knife holder 9 possesses a first and a second position 9a and 9b for insertion of a knife. A trimming knife 36 is inserted in first position 9a. Sample holder 7 is embodied rotatably. The sample clamped in sample holder 7 can thus, for example, be rotated 90°. Sample holder 7 is embodied with several openings 37 that serve for insertion of a tool (not depicted). With the tool, sample holder 7 can, for example, be rotated or even removed from cooling chamber 30.

Figure 3:
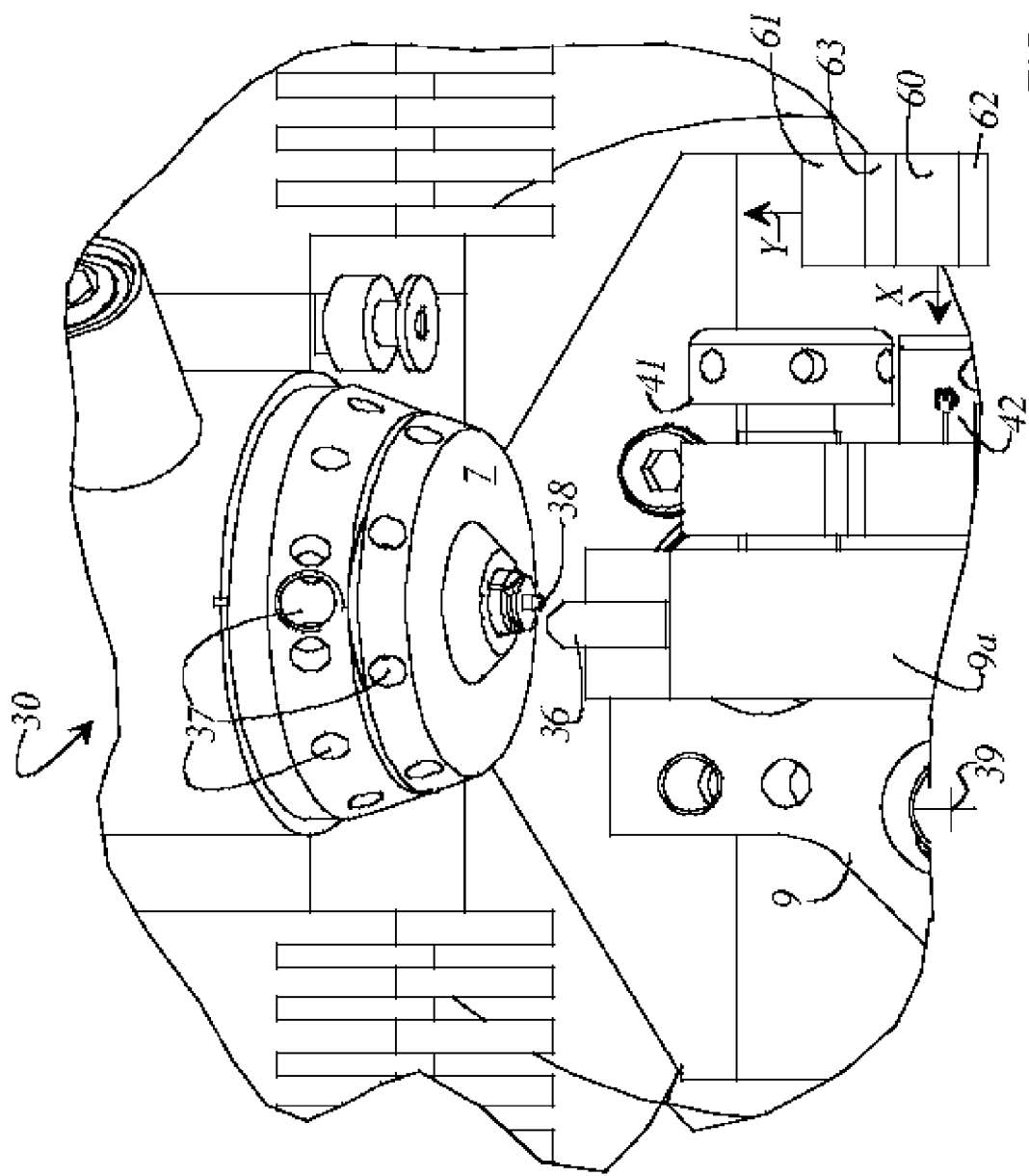
FIG. 3 shows a portion of the cooling chamber with the correlation between the trimming knife and the sample to be trimmed.

FIG. 3 shows a portion of cooling chamber 30 with the correlation between trimming knife 36 and a sample 38 to be trimmed. Sample 38 is retained in sample holder 7 in such a way that sample 38 is arranged opposite trimming knife 36. Trimming knife 36 is inserted in first position 9a of knife holder 7. Knife holder 7 is pivotable about an axis 39 so that after the trimming of sample 38, a sectioning knife (not depicted) can be pivoted into a position opposite the trimmed sample 38. Before the sectioning of samples with an ultramicrotome, the sample or specimen is trimmed. "Trimming" is understood to mean the preparatory cutting of the specimen to a size that allows thin sections to be produced in the ultramicrotome. In this context, the frontmost region, or region to be sectioned, of a sample 38 must not exceed a certain dimension. The limiting factors are the width of the sectioning knife blade, which is restricted to 6–10 mm in the case of a glass knife and to approximately 4 mm in the case of a diamond knife; and the slide grid for subsequent observation in an electron microscope. The slide screens possess a diameter of 3 mm. Sectioned sample surfaces larger than 1 mm square are seldom used in practice, since it is usually desirable to observe several sections on one slide grid. The trimming knife is retained in knife holder 9 in the first position by a first and a second adjusting screw 41, 42. Knife holder 9 is also movable in X direction X with a first motor 60, and in Y direction Y with a second motor 61. As depicted in FIG. 1, device 1 is equipped with a control unit 15 that controls and monitors, for example, the motion of knife holder 7 in the X direction and Y direction. In addition, the advance and total advance depth can be inputted via input unit 17 connected to control unit 15.

Figure 4:
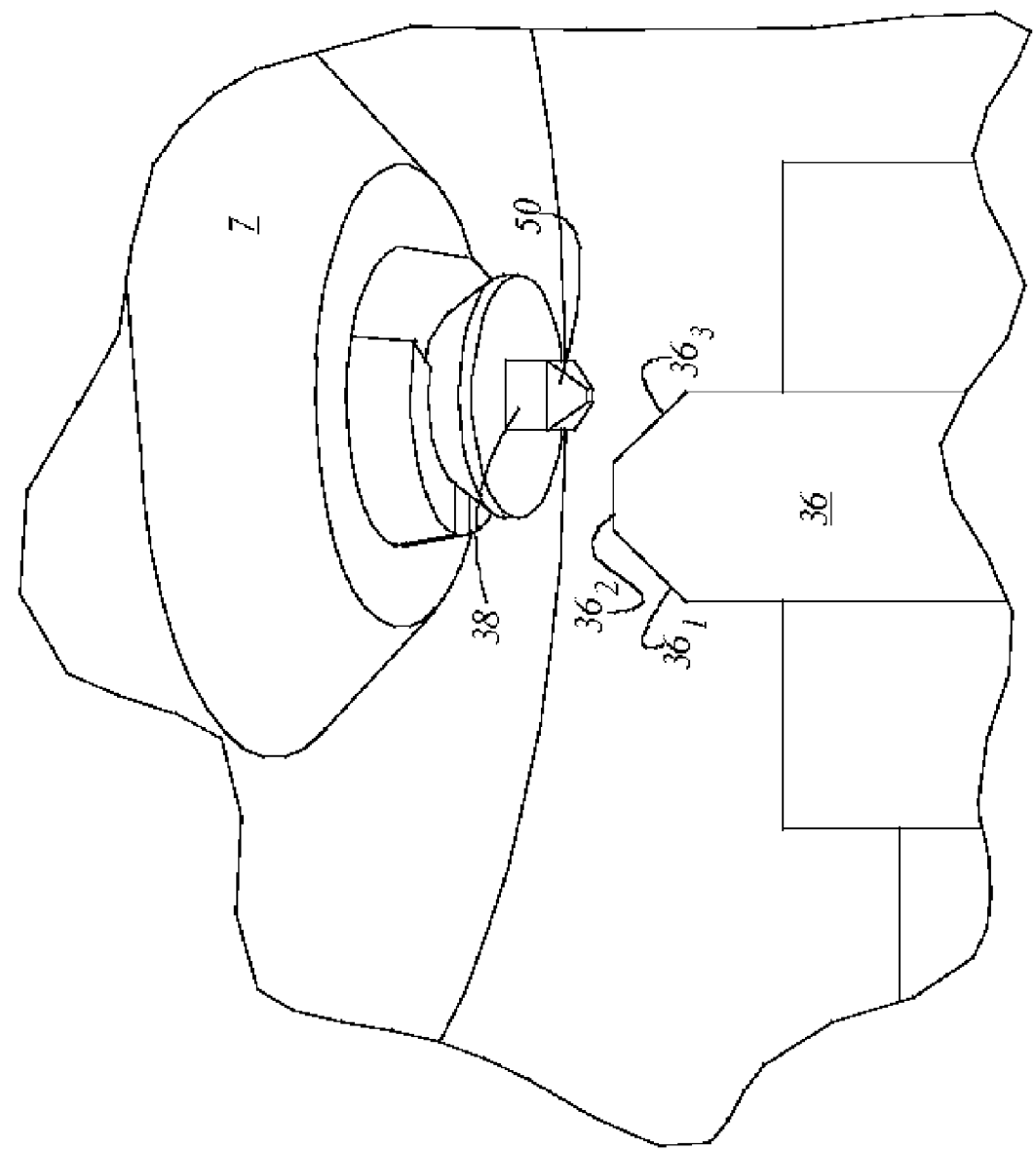
FIG. 4 is an enlarged depiction of the three-dimensional correlation between the trimming knife and the sample to be trimmed.

FIG. 4 is an enlarged depiction of the three-dimensional correlation between trimming knife 36 and sample 38 to be trimmed. Trimming knife 36 is embodied with a first cutting edge $36_1$, a second cutting edge $36_2$, and a third cutting edge $36_3$. First cutting edge $36_1$, second cutting edge $36_2$, and third cutting edge $36_3$ serve to generate surfaces $38_1$, $38_2$, $38_3$, $38_4$, and $38_5$ that constitute the trimmed sample 38. Surfaces $38_1$, $38_2$, $38_3$, $38_4$, and $38_5$ constitute, for the trimmed sample 38, the three-dimensional shape of a truncated pyramid 50. Second cutting edge $36_2$ of trimming knife 36 serves to produce fifth surface $38_5$ of truncated pyramid 50, which is referred to as the front surface. The position of trimming knife 36 and sample 38 shown in FIG. 4 is such that first surface $38_1$ of truncated pyramid 50 is being trimmed therewith.

Figure 5B:
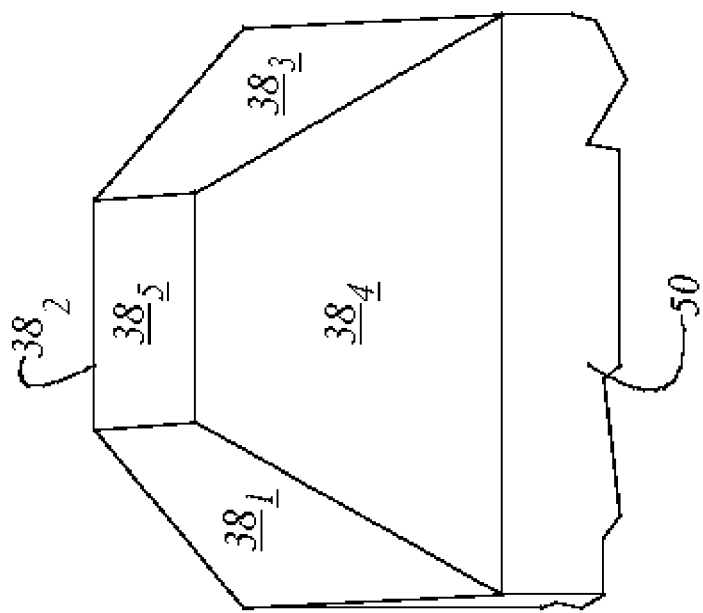
FIG. 5b depicts the three-dimensional arrangement of the trimmed surfaces on a sample.
Figure 5A:
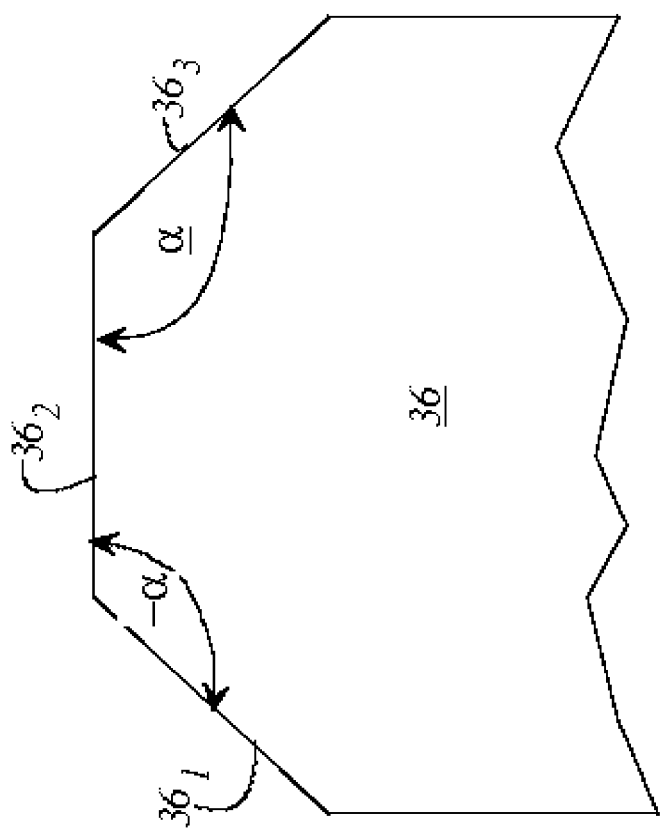
FIG. 5a depicts the arrangement of the first cutting edge, second cutting edge, and third cutting edge of the trimming knife.

FIG. 5a is an enlarged depiction of cutting edges $36_1$, $36_2$, and $36_3$. First cutting edge $36_1$ is inclined with respect to second cutting edge $36_2$ at an angle $-\alpha$, and third cutting edge $36_3$ is inclined with respect to second cutting edge $36_2$ at an angle $\alpha$. FIG. 5b is an enlarged depiction of truncated pyramid 50 that is formed by a shaping process using first cutting edge $36_1$, second cutting edge $36_2$, and third cutting edge $36_3$. Truncated pyramid 50 is constituted by a four-sided pyramid whose tip has been cut off. Truncated pyramid 50 is also constituted by first side surface $38_1$, second side surface $38_2$, third side surface $38_3$, fourth side surface $38_4$, and front surface $38_5$. The shape of truncated pyramid 50 is determined by the angle between first and third cutting edges $36_1$, $36_3$ and second cutting edge $36_2$. Right-angle trimming knifes are also common. In this case first and third cutting edges $36_1$, $36_3$ form a right angle with second cutting edge $36_2$. A cube rather than a truncated pyramid 50 is then created at the tip of the sample.

Figure 6:
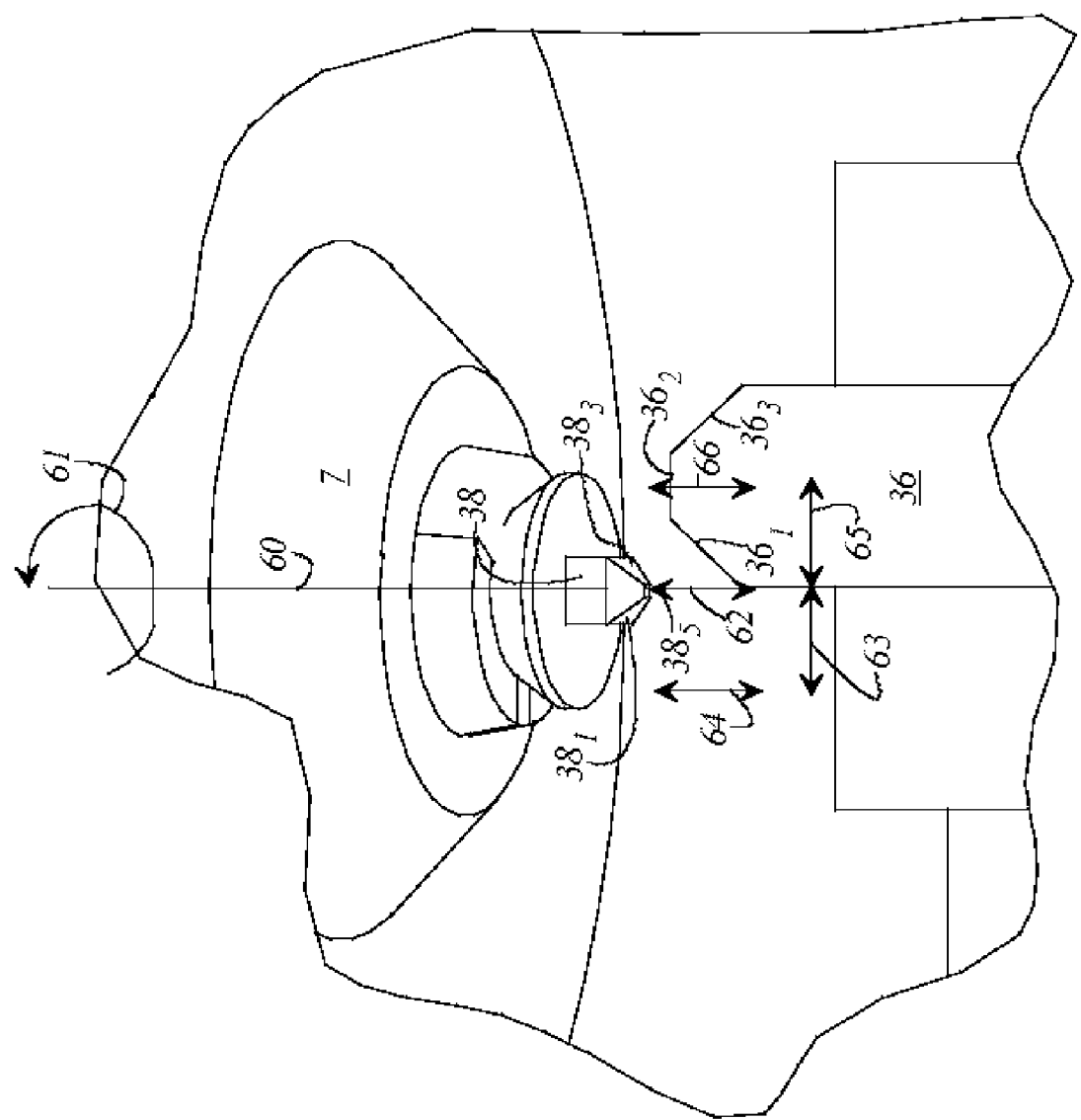
FIG. 6 shows a position for trimming the first side surface of the sample, the arrows illustrating the motion sequence of the trimming knife.

FIG. 6 shows a position for trimming third side surface $38_3$ of truncated pyramid 50 of sample 38. The arrows depicted illustrate the motion sequence of trimming knife 36. Trimming takes place in cooling chamber 30. Trimming knife 36 is used both to shape sample 38 laterally and thus to form the desired side surfaces of truncated pyramid 50, and to cut across front surface $38_5$.

After a rotation of the specimen, the two side surfaces are shaped in turn. Rotation of the specimen about an axis 60 of specimen holder 7 is indicated in FIG. 6 by an arrow 61. A rectangular precut surface or front surface $38_5$ is thereby created. The individual steps with which truncated pyramid 50 is produced will be described below. Firstly, trimming knife 36 is brought close to sample 38. Precutting of the front surface is then performed. This yields a front surface that is aligned parallel to second cutting edge $36_2$. This is indicated in FIG. 6 by double arrow 62. Once precutting is achieved, the advance is reversed (also double arrow 62). Advance of the specimen is limited to approximately 200 μm. A lateral displacement of trimming knife 36 (indicated by double arrow 63 in FIG. 6) is then performed, and trimming knife 36 is preset. Trimming of first side surface $38_1$ of truncated pyramid 50 (left side of sample) is performed, and an advance of 1 μm is usually selected. The advance is depicted with double arrow 64 in FIG. 6. The motions of the trimming knife are depicted as double arrows, which is intended to indicate that the motion can occur in both directions. Cutting is performed in this context to a depth of approximately 100 μm. First side surface $38_1$ of truncated pyramid 50 (left side of sample) is cut with third cutting edge $36_3$ of trimming knife 36. Once this is complete, the advance is reversed. A lateral displacement of trimming knife 36 to the right is then performed, as indicated by the successive double arrows 63 and 65. Trimming knife 36 is once again preset. Trimming of third side surface $38_3$ is then performed (usually 1-μm cuts to a depth of approximately 100 μm). This trimming is illustrated by double arrow 66; cutting occurs to a depth of approximately 100 μm. Third side surface $38_3$ of truncated pyramid 50 (right side of sample) is cut with first cutting edge $36_1$ of trimming knife 36. Once this is completed, the advance is reversed. Lastly, trimming knife 36 is pulled back. Sample 38 is then rotated 90° (see arrow 61). Trimming knife 36 is preset. Trimming of second side surface $38_2$ of truncated pyramid 50 (left side of sample) is performed; an advance of 1 μm is usually selected and, as already mentioned, cutting occurs to a depth of approximately 100 μm. Once this is completed, the advance is reversed. Second side surface $38_2$ of truncated pyramid 50 (left side of sample) is cut with first cutting edge $36_1$ of trimming knife 36. A lateral displacement of trimming knife 36 to the left is then performed. Trimming knife 36 is once again preset. Trimming of fourth side surface $38_4$ is then performed (usually 1-μm cuts to a depth of approximately 100 μm). Once this is completed, the advance is reversed. Fourth side surface $38_4$ of truncated pyramid 50 (left side of sample) is cut with third cutting edge $36_3$ of trimming knife 36.

In order to automate this operation of trimming sample 38, the X-Y displacement of trimming knife 36 is motorized and equipped with a position measurement capability. This can be accomplished, for example, by means of stepping motors and by counting the steps for position determination. It is advantageous if advance occurs on the knife side for trimming. The "reverse the specimen advance" steps can then be omitted, since the displacement range of the knife is several millimeters, while that of the specimen advance is only 200 μm. The automated operation of trimming sample 38 possesses the following steps:

Firstly an X-Y displacement of trimming knife 36 to the starting point is performed, the knife being moved against the left side of sample 38. This position is stored by pressing a button on input unit 17 of control unit 15. The trimming depth is likewise inputted by means of input unit 17 of control unit 15. Trimming knife 36 is moved by X-Y displacement to the starting point against front surface $38_5$ of sample 38. This position is likewise stored by pressing a button. The trimming depth is inputted. Trimming knife 36 is moved by X-Y displacement to the starting point against the right side of sample 38. This position is stored by pressing a button on input unit 17 of control unit 15. The trimming depth is inputted. Actuation of the start button causes the above-described operation of trimming sample 38 to proceed automatically. After each trimming operation, the next stored position is moved to and the trimming operation is started again. Once first side surface $38_1$ and third side surface $38_3$ of the sample have been trimmed, a 90° rotation of the sample is performed. Trimming knife 38 is moved by X-Y displacement to the starting point against the right side of the sample. This position is stored by pressing a button. The trimming depth is inputted at input unit 17 of control unit 15. Trimming knife 38 is moved by X-Y displacement to the starting point against the left side of sample 38. This position is stored by pressing a button. The trimming depth is inputted at input unit 17 of control unit 15. Actuation of the start button on input unit 17 of control unit 15 causes the operation described above to proceed automatically. The operation causes second side surface $38_2$ and fourth side surface $38_4$ of truncated pyramid 50 to be shaped.

What is claimed is:

1. A device for trimming samples in a microtome, comprising:
   a knife holder and a rotatable sample holder, wherein the knife holder carries at least one trimming knife and a cutting knife;
   a cooling chamber surrounding the sample holder and the knife holder;

a first motor that moves the knife holder in the X direction;

a second motor that moves the knife holder in the Y direction;

a control unit associated with the device, wherein the control unit controls the motion of the knife holder in the X direction and the motion of the knife holder in the Y direction; and, a measurement means with the first and the second motor which measures the position of the knife holder in the X direction and Y direction, wherein, for a sample held by the sample holder, the trimming knife is arranged to form a first surface orthogonal to an axis of rotation for the sample holder and to form four additional flat surfaces bordering the first surface and wherein said trimming knife possesses at least two cutting edges.

2. The device as defined in claim 1, wherein the first and the second motor are embodied as stepping motors; and the measurement means determining the position of the knife holder counts the steps of the first and the second motor in the X direction and Y direction.

3. The device as defined in claim 1, wherein the trimming knife possesses a first cutting edge, a second cutting edge, and a third cutting edge.

4. The device as defined in claim 3, wherein the second cutting edge generates a front surface of the sample, the second cutting edge being parallel to the front surface of the sample.

5. The device as defined in claim 3, wherein the first cutting edge generates at least one right side surface of the sample.

6. The device as defined in claim 3, wherein the third cutting edge generates at least one left side surface of the sample.

7. The device as defined in claim 4, wherein the first cutting edge meets the second cutting edge at a first angle; and the second cutting edge meets the third cutting edge at a second angle.

8. The device as defined in claim 7, wherein the first and second angles are obtuse angles, respectively.

9. The device as defined in claim 8, wherein the trimming knife, in which the first cutting edge and second cutting edge as well as the second cutting edge and third cutting edge meet at an oblique angle, generates in the sample a truncated pyramid at a tip of the sample.

10. The device as defined in claim 7, wherein the first and second angles are right angles, respectively.

11. The device as defined in claim 10, wherein the trimming knife, in which the first cutting edge and second cutting edge as well as the second cutting edge and third cutting edge meet at a right angle, generates in the sample a cube at the tip of the sample.

12. The device as defined in claim 11, wherein the knife holder exhibits a first and a second position, the trimming knife being used in the first position and a sectioning knife in the second position.

13. The device as defined in claim 12, wherein the knife holder is pivotable about an axis so that after trimming of the sample, the sectioning knife is pivotable into a position opposite the trimmed sample with no need to remove the knife holder from the cooling chamber.

* * * * *